(12) United States Patent
Kim et al.

(10) Patent No.: US 6,399,777 B2
(45) Date of Patent: Jun. 4, 2002

(54) INCLUSION COMPLEXES OF ARYL-HETEROCYCLIC SALTS

(75) Inventors: Yesook Kim, Branford; Kevin C. Johnson, Niantic; Ravi M. Shanker, Groton, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/850,658

(22) Filed: May 7, 2001

Related U.S. Application Data

(62) Division of application No. 09/147,239, filed as application No. PCT/IB97/00321 on Apr. 1, 1997, now Pat. No. 6,232,304.
(60) Provisional application No. 60/019,204, filed on May 7, 1996.

(51) Int. Cl.[7] ............................................. C07D 417/14
(52) U.S. Cl. ...................................................... 544/368
(58) Field of Search ......................................... 544/368

(56) References Cited

U.S. PATENT DOCUMENTS

| 4,603,123 | A | | 7/1986 | Chiesi et al. ................... 514/58 |
|---|---|---|---|---|
| 4,831,031 | A | | 5/1989 | Lowe, III et al. ............ 514/253 |
| 4,883,795 | A | | 11/1989 | Lowe, III et al. ............ 514/253 |
| 5,134,127 | A | | 7/1992 | Stella et al. .................... 514/58 |
| 5,312,925 | A | | 5/1994 | Allen et al. ................. 544/368 |
| 5,376,645 | A | | 12/1994 | Stella et al. .................... 514/58 |
| 5,756,546 | A | | 5/1998 | Pirotte et al. ................. 514/605 |
| 5,904,929 | A | * | 5/1999 | Uekama et al. ............... 424/443 |
| 6,110,918 | A | | 8/2000 | Busch et al. .................. 514/255 |
| 6,245,765 | B1 | | 6/2001 | Busch et al. ............ 514/252.13 |

FOREIGN PATENT DOCUMENTS

| EP | 0281309 | 9/1988 | ......... C07D/263/58 |
|---|---|---|---|
| EP | 0586191 | 3/1994 | ......... C07D/417/12 |
| EP | 0811386 | 4/1997 | .......... A61K/47/48 |
| EP | 0281309 | 9/1998 | ......... C07D/263/58 |
| WO | WO9402177 | 2/1994 | .......... A61K/47/48 |
| WO | WO9402518 | 2/1994 | .......... C08B/37/16 |
| WO | WO9416733 | 8/1994 | .......... A61K/47/48 |
| WO | WO9428031 | 12/1994 | .......... C08B/37/16 |
| WO | WO9528965 | 11/1995 | .......... A61K/47/48 |
| WO | WO9742190 | 11/1997 | ......... C07D/417/12 |
| WO | WO9742191 | 11/1997 | ......... C07D/417/12 |

OTHER PUBLICATIONS

EP698018–A1 Abstract.
Pharmaceutical Technology, 8, pp. 22–26 (1990) Pshysicochemical Characteristics and Pharmaceutical Uses of Cyclodextrin Derivatives, Part II.

* cited by examiner

*Primary Examiner*—Robert Gerstl
(74) *Attorney, Agent, or Firm*—Peter C. Richardson; Gregg C. Benson; James T. Jones

(57) ABSTRACT

The esylate, mesylate, and tartrate salts of ziprasidone exhibit excellent solubilities in cyclodextrins.

4 Claims, 1 Drawing Sheet

INCLUSION COMPLEXES OF ARYL-HETEROCYCLIC SALTS

CROSS-REFERENCE TO RELATED APPLICATIONS

This is a division of U.S. Ser. No. 09/147,239, filed Nov. 5, 1998 now U.S. Pat. No. 6,232,364 entitled "Inclusion Complexes of Aryl-Heterocyclic Salts", which is a National Stage filing under 35 USC §371 based on PCT/IB97/00321 which was filed internationally on Apr. 1, 1997 and which claimed priority to U.S. Provisional Application No. 60/019,204 filed May 7, 1996.

FIELD OF THE INVENTION

This invention relates to compositions comprising a salt of an arylpiperazinyl-$C_2$ or -$C_4$ alkyleneheterocycle and a cyclodextrin.

BACKGROUND OF THE INVENTION

Formulation of pharmaceutical dosage forms is frequently hampered by poor aqueous solubility and/or stability of the drug of interest, which in turn can severely limit its therapeutic application. Conversely, increasing drug solubility and stability through appropriate formulation can accordingly lead to increased therapeutic efficacy of the drug. Various methods have been used to increase the solubility and stability of drugs such as the use of organic solvents, emulsions, liposomes and micelles, adjustments to pH and the dielectric constant of formulations solvent systems, chemical modifications, and complexation of the drugs with appropriate complexing agents such as cyclodextrins.

Cyclodextrins, sometimes referred to as Schardinger's dextrins, were first isolated by Villiers in 1891 as a digest of *Bacillus amylobacter* on potato starch. The foundations of cyclodextrin chemistry were laid down by Schardinger in the period 1903–1911. Until 1970, however, only small amounts of cyclodextrins could be produced in the laboratory and the high production cost prevented the usage of cyclodextrins in industry. In recent years, dramatic improvements in cyclodextrin production and purification have been achieved and cyclodextrins have become much less expensive, thereby making the industrial application of cydodextrins possible.

Cyclodextrins are cyclic oligosaccharides with hydroxyl groups on the outer surface and a void cavity in the center. Their outer surface is hydrophilic, and therefore they are usually soluble in water, but the cavity has a lipophilic character. The most common cyclodextrins are α-cyclodextrin, β-cyclodextrin and γ-cyclodextrin, consisting of 6; 7 and 8 α-1,4-linked glucose units, respectively. The number of these units determines the size of the cavity.

Cyclodextrins are capable of forming inclusion complexes with a wide variety of hydrophobic molecules by taking up a whole molecule (a "guest molecule"), or some part of it, into the void cavity. The stability of the resulting complex depends on how well the guest molecule fits into the cyclodextrin cavity. Common cyclodextrin derivatives are formed by alkylation (e.g., methyl-and-ethyl-β-cydodextrin) or hydroxyalkylation of the hydroxyethyl-derivatives of α-, β-, and γ-cyclodextrin) or by substituting the primary hydroxyl groups with saccharides (e.g., glucosyl- and maltosyl- β-cyclodextrin). Hydroxypropyl-β-cyclodextrin and its preparation by propylene oxide addition to β-cyclodextrin, and hydroxyethyl-β-cyclodextrin and its preparation by ethylene oxide addition to β-cyclodextrin, were described in a patent of Gramera et al. (U.S. Pat. No. 3,459,731, issued August 1969) over 20 years ago.

Although cyclodextrins have been used to increase the solubility, dissolution rate and/or stability of a great many compounds, it is also known there are many drugs for which cyclodextrin complexation either is not possible or yields no advantages. See J. Szejtli, Cyclodextrins in Drug Formulations: Part II, Pharmaceutical Technology, 24–38, August, 1991.

It is conventionally believed that a salt of a drug dissolves in a cyclodextrin-containing aqueous medium by simply dissociating to form a charged drug molecule and a counter-ion, and that it is the dissociated (charged) drug molecule which acts as a guest moiety and forms inclusion complexes with the cyclodextrin. A consequence of this is the belief that there are no differences in equilibrium solubility among the salts of a given drug in a specific cyclodextrin. Thus, if a solubility-phase diagram is generated for a particular drug in a particular aqueous cyclodextrin (i.e., a plot of the equilibrium solubility of a drug salt in the aqueous cyclodextrin as a function of cyclodextrin concentration), different salts of the drug should plot out as lines having the same slope.

The present invention is based, inter alia, on the determination that the solubility of the compounds presented below form stable inclusion complexes with cyclodextrins, and that such inclusion complexes are highly water soluble relative to the non-complexed drug.

The present invention is further based on the unexpected and surprising discovery that, in a particular cyclodextrin, there are solubility differences among particular salts of the aryl-heterocyclics useful herein. A particular salt of a specific aryl-heterocyclic can exhibit much greater solubility in a particular aqueous cycdodextrin solution than a different salt of the same aryleterocycle in the same cyclodextrin. Some salts show unexpectedly high solubility. Many, if not all, of the salts investigated for this invention exhibited their own distinctive slope when plotted on a solubility-phase diagram.

In the particular case of the aryl-heterocyclic ziprasidone, it has been determined that the order of solubility (e.g., the increasing order of solubility) of a series of different ziprasidone salts in aqueous cyclodextrin solution does not necessarily correlate with the order of solubility of those same salts in water.

SUMMARY OF THE INVENTION

In one embodiment this invention provides compositions of matter comprising a cyclodextrin and a pharmaceutically acceptable salt of a compound (herein referred to as an "aryl-heterocyclic") having the formula

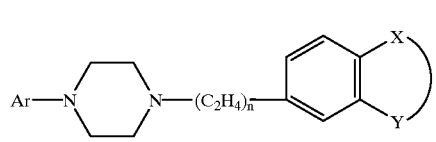

I wherein
  Ar is benzoisothiazolyl or an oxide or dioxide thereof each optionally substituted by one fluoro, chloro, trifluoromethyl, methoxy, cyano, or nitro;
  n is 1 or 2; and
  X and Y together with the phenyl to which they are attached form benzothiazolyl; 2-aminobenzothiazolyl;

benzoisothiazolyl; indazolyl; 3-hydroxyindazolyl; indolyl; oxindolyl optionally substituted by one to three of ($C_1$–$C_3$)alkyl, or one of chloro, fluoro or phenyl, said phenyl optionally substituted by one chloro or fluoro; benzoxazolyl; 2-aminobenzoxazolyl; benzoxazolonyl; 2-aminobenzoxazolinyl; benzothiazolonyl; benzoimidazolonyl; or benzotriazolyl. The preceding compounds are disclosed in U.S. Pat. No. 4,831,031, herein incorporated by reference in its entirety.

A preferred subgroup of the above compositions is the subgroup wherein X and Y together with the phenyl to which they are attached form oxindole; A preferred subgroup within this subgroup occurs when the oxindole moiety is 6-chlorooxindole-5-yl.

A further preferred subgroup of compositions is the subgroup wherein Ar is benzoisothiazolyl.

A further preferred subgroup of compositions is the subgroup wherein n is 1.

A preferred aryl-heterocyclic is ziprasidone, which has the structure

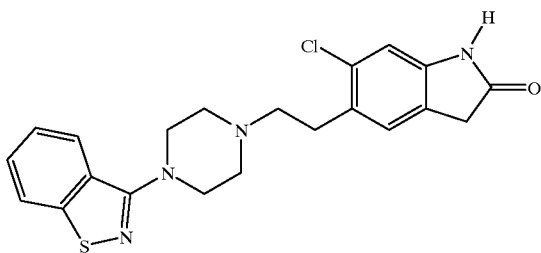

It is also disclosed in the previously mentioned U.S. Pat. No. 4,831,031, has utility as a neuroleptic, and is thus useful as an antipsychotic.

Further preferred compositions of matter comprise a pharmaceutically acceptable salt of ziprasidone and a cyclodextrin,
wherein said salt is selected from the tosylate, tartrate, napsylate, besylate, aspartate, esylate and mesylate salt; and wherein said cyclodextrin is selected from γ-cyclodextrin, SBECD and HPBCD.

This invention thus provides compositions of matter comprising a pharmaceutically acceptable salt of an aryl-heterocyclic and a cyclodextrin. The compositions can be administered orally, for example as a tablet or capsule, or parenterally, for example, as an injectable or by inhalation to a mammal in need thereof, The phrase "composition(s) of matter" as used herein including the appendant claims encompasses, inter alia, compositions of an aryl-heterocyclic and a cyclodextrin which are dry physical mixtures, which are dry inclusion complexes, and which are aqueous solutions of dissolved inclusion complexes. For example, a composition can comprise a dry mixture of an aryl-heterocyclic physically mixed with a dry cydodextrin. A composition, in a preferred embodiment, can also comprise an aqueous solution which has been lyophilized or otherwise dried (e.g., in a vacuum oven or other suitable device), such that the composition comprises a dry, pre-formed inclusion complex of cyclodextrin-complexed aryl-heterocyclic which can later be re-constituted. A composition can also comprise the aqueous solution itself, i.e., an aryl-heterocyclic plus cyclodextrin plus water. Inclusion complexes are thus within the scope of the term "composition of matter" whether they are preformed, formed in situ, or formed in vivo.

The aryl-heterocyclic salt is advantageously relatively highly soluble in aqueous cyclodextrin solution, and if administered to a patient parenterally as an aqueous solution, can accordingly be administered in a relatively small injection volume.

Physical mixtures of a cyclodextrin and an aryl-heterocyclic are usefully employed and are within the scope of this invention. A mixture of a cyclodextrin and an aryl-heterocyclic, for example used as fill for a capsule or compressed into a tablet for oral administration, will form an inclusion complex on exposure to an aqueous environment of use such as the luminal fluid of the gastrointestinal tract or the salivary fluid of the buccal cavity, and thereby aid in increasing bioavailability relative to the uncomplexed drug. Cyclodextrin can be present in an amount over that needed to complex the drug completely since extra cyclodextrin aids in dissolution of the dosage form once it contacts aqueous fluid.

In a further aspect, this invention provides compositions of matter suitable for administration to a human patient as a solution (e.g., as an injectable or intranasally), comprising an inclusion complex of a salt of ziprasidone in a cyclodextrin. Advantageously, in a preferred embodiment said inclusion complex provides an amount of ziprasidone of at least 2.5 mgA/ml when the amount of ziprasidone (or other aryl-heterocyclic) provided by said complex is measured at a cyclodextrin concentration of 40% w/v in water.

Inclusion complexes that provide at least 10 mgA/ml of ziprasidone at 40% w/v in water are more preferred.

Inclusion complexes that provide at least 15 mgA/ml of ziprasidone at 40% w/v are most preferred.

As a further feature of the invention, the mesylate, esylate, and tartrate salts of ziprasidone are provided.

The phrase "mgA" indicates the weight (in mg) of ziprasidone (or other aryl-heterocyclic) calculated as the free base, (for ziprasidone, molecular weight=412.9).

The phrase "measured at a cyclodextrin concentration of 40% w/v in water" as used above and in the claims provides a standard against which the degree of solubility of a particular inclusion complex of ziprasidone in a particular cyclodextrin, and hence its usefulness, can be compared. The phrase is not to be interpreted as limiting the invention in any way. For example, assume that a test solution of a particular cyclodextrin X in water is made up to 40% w/v ("w/v" being based, of course, on the weight "w" of the cyclodextrin in water, "v" referring to the total solution volume), and that this test solution, at equilibrium solubility, provides a concentration of 10 mgA/ml of ziprasidone salt Y. The (dry or non-solvated) inclusion complex (i.e., of ziprasidone salt Y in cyclodextrin X) used to make the 40% test solution thus represents a preferred inclusion complex because it exceeds the standard of 2.5 mgA/ml. Assuming that the solubility phase diagram for ziprasidone salt X is linear and passes through the origin, an inclusion complex of salt Y in the same cyclodextrin X, for example at an aqueous cyclodextrin concentration of 20% w/v, will provide 5 mgA/ml. The inclusion complex used to make this second solution is equally preferred even though a different concentration of cyclodextrin in water was employed to make the ziprasidone salt solubility measurement.

Viewed alternatively, an aqueous cyclodextrin test concentration of 40% w/v provides a point at which a determination can be made regarding whether a cyclodextrin inclusion complex of a particular ziprasidone salt in a particular cyclodextrin can provide at least 2.5 mgA/ml of ziprasidone. If such determination is positive, any inclusion complex made with that salt and that cyclodextrin is preferred.

Use of the term "salt" herein, including the appendant claims, shall be understood to refer to pharmaceutically acceptable acid addition salts of aryl-heterocyclics, including ziprasidone. The salts employed can be anhydrous or in the form of one or more solvates, such as hydrates, including mixtures thereof. The salts may occur in different polymorphic forms. For example, co-pending U.S. provisional application 60/1016537, herein incorporated by reference, discloses the mesylate trihydrate salt of ziprasidone. Co-pending U.S. provisional application 60/016757, herein incorporated by reference, discloses the mesylate dihydrate salt of ziprasidone.

"Product solution" as used herein, including the appendant claims, means an aqueous solution of a salt of an aryl-heterocyclic (including ziprasidone) inclusion complex in a cyclodextrin, which solution is pharmaceutically acceptable and ready for administration to a patient.

The fact that different aryl-heterocyclic salts can exhibit differing solubilities in a particular aqueous cyclodextrin solution is applicable to cyclodextrins in general, including those which are presently known. Useful cyclodextrins include α, β, and γ cyclodextrins, methylated cyclodextrins, hydroxypropyl-β-cyclodextrin (HPBCD), hydroxyethyl-β-cyclodextrin (HEBCD), branched cyclodextrins in which one or two glucoses or maltoses are enzymatically attached to the cyclodextrin ring, ethyl- and ethyl-carboxymethyl cyclodextrins, dihydroxypropyl cyclodextrins, and sulfoalkyl ether cyclodextrins. The degree of substitution is not considered to be critical, and the cyclodextrins just mentioned can have essentially any degree of substitution (per entire cyclodextrin molecule) as known in the art. Mixtures of cyclodextrins, as well as single species, are feasible for making dosage forms according to the invention.

β-cyclodextrin sulfobutyl ether (SBECD), hydroxypropyl β-cyclodextrin (HPBCD), and γ-cyclodextrin are preferred for use in this invention. HPBCD and SBECD are preferred for parenteral administration. For oral administration γ-cyclodextrin is preferred. HPBCD is well known in the art, see for example Publication R 81 216 entitled "Encapsin HPB" from Janssen Biotech N.V. SBECD is also known and has been disclosed in U.S. Pat. Nos. 5,376,645 and 5,134,127, both to Stella et al. and both herein incorporated by reference in their entirety.

A preferred group of inclusion complexes of ziprasidone salts includes (1) the tosylate, napsylate, besylate, aspartate, tartrate, esylate (ethanesulfonate) or mesylate (methanesulfonate) salts of ziprasidone, each complexed with SBECD; and (2) the tartrate, esylate, or mesylate salts of ziprasidone, each complexed with HPBCD.

A more preferred group of inclusion complexes of ziprasidone salts includes (1) the tosylate, napsylate, besylate, tartrate, esylate or mesylate salts of ziprasidone, each complexed with SBECD; and (2) the tartrate, esylate, or mesylate salts of ziprasidone, each complexed with HPBCD.

A still more preferred group of inclusion complexes of ziprasidone salts includes (1) the tartrate, esylate, or mesylate salts of ziprasidone, each complexed with SBECD; and (2) the tartrate, esylate or mesylate salts of ziprasidone, each complexed with HPBCD.

A still more preferred group of inclusion complexes of ziprasidone salts include ziprasidone mesylate or tartrate, each complexed with SBECD.

Most preferred is ziprasidone mesylate complexed with SBECD.

The inclusion complexes of this invention can be administered orally and parenterally, as previously noted.

As previously noted, this invention is based, inter alia, on the determination that, for a particular cyclodextrin, the solubility of an aryl-heterocyclic salt such as a ziprasidone salt in that cyclodextrin is dependent on the particular salt employed. That is, different aryl-heterocyclic salts, including ziprasidone, exhibit (sometimes widely) differing solubilities in the same cyclodextrin. This phenomenon of variable solubility is particularly important for parenteral administration because it allows for increasing the loading of an aryl-heterocydic in a cyclodextrin by selecting a salt with relatively high cyclodextrin solubility. Increased loading in turn allows for the capability of parenterally delivering a given dose of aryl-heterocyclic in a relatively decreased injection volume. Viewed alternatively, since the weight of cyclodextrin required to dissolve a given weight of an aryl-heterocyclic decreases with increasing salt solubility in an aqueous solution of the cyclodextrin, and assuming a constant loading of ziprasidone, injection volume can be reduced by choosing an appropriate, highly soluble salt. It is well known in the medical arts that pain on injection can increase in proportion to the injection volume employed. Patient compliance with parenteral administration can be affected accordingly. Thus the ability to administer ziprasidone in a decreased injection volume represents a significant advance in this art. For example, in many cases, this invention provides therapeutic solutions of a ziprasidone inclusion complex which provide the maximum once-daily level of ziprasidone in a single injection volume less than 2 ml.

Figure 1:
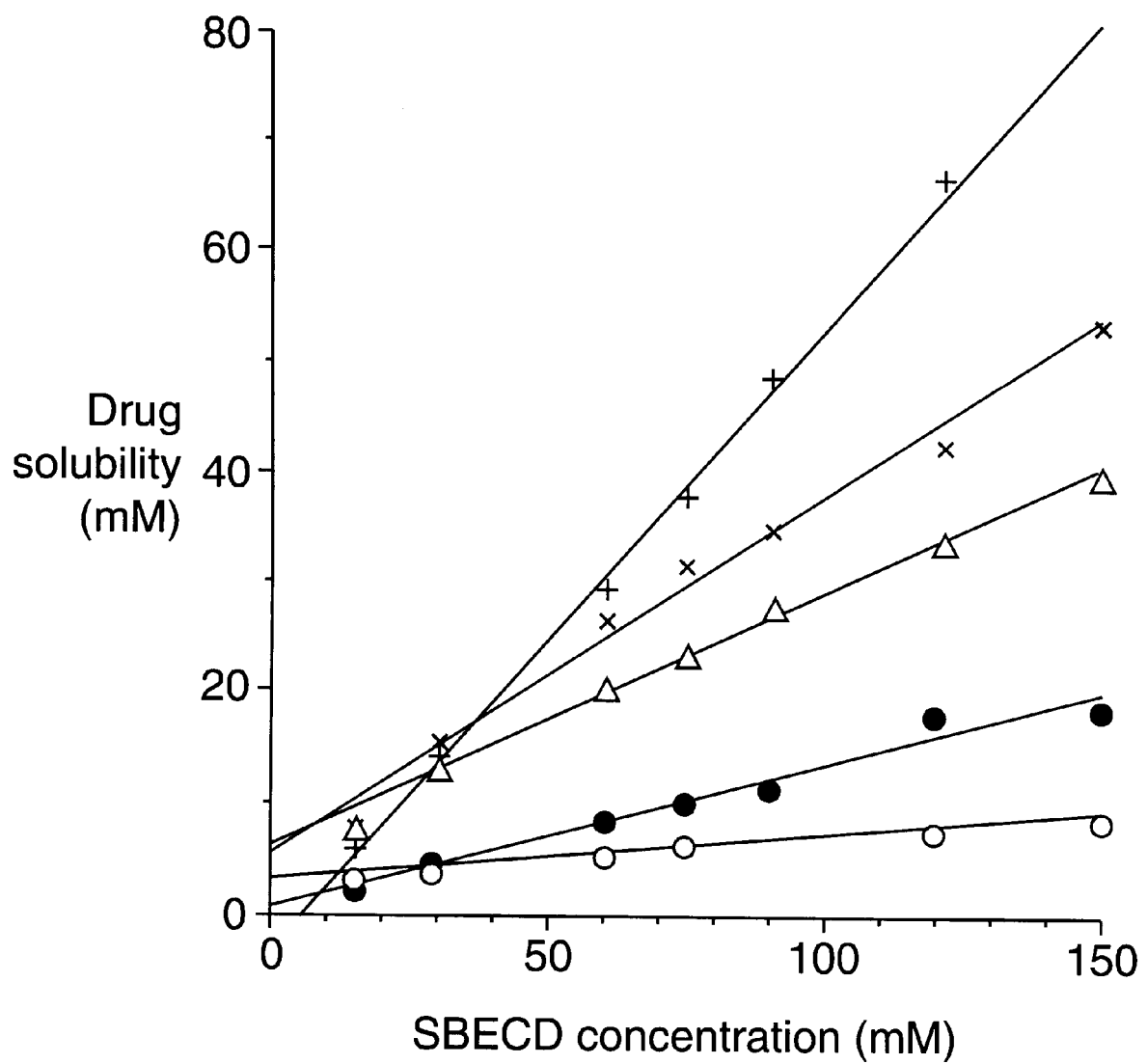
FIG. 1 is a solubility phase diagram which is a plot of the maximum equilibrium solubility of a series of ziprasidone salts as a function of SBECD concentration in water.

The ordinate (Y-axis) is Drug Solubility (units are millimolar) and the abscissa (X-axis) is SBECD concentration (also millimolar units).

The symbology employed is explained in the following chart:

| | Salt |
|---|---|
| + | Mesylate |
| X | Tartrate |
| Δ | Esylate |
| • | Napsylate |
| O | HCl |

DETAILED DISCUSSION

The amount of aryl-heterocyclic to be administered to a patient is an effective amount, generally from 5 to 500 mgA, in single or divided doses, orally or parenterally. The specific dose administered will depend on the particular condition being treated. With respect to ziprasidone specifically, a recommended range for oral dosing is 5–300 mgA/day, preferably 40–200 mgA/day, more preferably 40–80 mgA in single or divided doses. A generally recommended therapeutic range for administering ziprasidone parenterally by injection is 2.5 mgalday to 160 mgA/day, preferably 5–80 mgA/day depending on several factors such as the size and condition of the patient. The ability to generate an aqueous cyclodextrin complex which provides at least 2.5 mgA/ml of ziprasidone means that the lower end of the above parenteral therapeutic ranges (2.5 mgA/day and 5 mgA/day) can be met by a single or by a divided, twice-per-day dose, with each administration comprising an injection of 1 ml at 2.5 mgA/ml. It will be demonstrated below that the invention provides inclusion complexes with the ability to deliver much greater concentrations of ziprasidone as well.

The amount of cyclodextrin used in a particular formulation is a bioavailability-increasing amount. Small amounts of cyclodextrin even when present in a dosage form which is a mixture, can enhance bioavailability by forming an inclusion complex in vivo. Generally the amount of cyclodextrin in a formulation is such that the molar ratio of cyclodextrin to drug is between 0.1:1 and 100:1, preferably between 0.25:1 and 10:1, more preferably between 0.5:1 and 5:1. If the formulation is an aqueous solution, it can contain cyclodextrin in a wide range of concentrations, e.g., from 5 wgt % (wtv) to over 100 wgt % (w/v). At high concentrations of cyclodextrins, formulations become somewhat viscous and are amenable to oral administration as elixirs or syrups.

The invention, as previously mentioned, is applicable to aryl-heterocyclics of formula I, as previously defined. For convenience, however, the following discussion is directed to ziprasidone as a representative member of the class of aryl-heterocyclics. Those skilled in the art will of course recognize that the teachings with respect to ziprasidone are applicable to the other members of the class as well.

The pharmaceutically acceptable acid addition salts of ziprasidone can be prepared as known in the art by conventional methodology by treating a solution or suspension of ziprasidone free base with about one chemical equivalent or a slight excess of a pharmaceutically acceptable acid. The salt can be isolated by conventional methods, such as by filtration when the salt spontaneously precipitates, e.g., as a crystalline material or, particularly if the salt is amorphous, it can be isolated by concentration and/or addition of a non-solvent. For example, the salts employed in this invention were made by first weighing an amount of ziprasidone free base and adding it to a solvent, typically tetrahydrofuran (THF), water, a lower alcohol, or a mixture of two or more solvents. The solvent(s) used can depend on whether it is desired to isolate the salt from a slurry or from a solution. If it is desired to isolate the salt from a solution, the solvent can be heated, with stirring, to between 60 and 70° C. to facilitate dissolution. Then about one molar equivalent of an acid, or a slight excess (usually up to 1.5:1, acid:base) corresponding to the desired counterion is added with stirring. Heating is maintained, usually for about two hours or longer, and then the solution is allowed to cool to room temperature for several hours, typically overnight, while stirring is maintained. The solids can then be harvested by filtration and washed with the cooled solvent composition.

An inclusion complex of a pharmaceutically acceptable acid addition salt of ziprasidone can be formed conventionally by known methodology. That is, a desired inclusion complex of a pharmaceutically acceptable ziprasidone salt can be formed in situ by adding a ziprasidone salt, in an amount up to the amount corresponding to its equilibrium solubilty (or less depending on the desired strength of the product solution), directly to a pre-made solution of cyclodextrin dissolved in water (or other suitable pharmaceutically acceptable aqueous medium). A combination comprising water (or other pharmaceutically acceptable aqueous medium such as a buffer), cyclodextrin, and a ziprasidone salt dissolved therein is sufficient to form a product solution which can be parenterally administered directly to human patients. A product solution made with sterile water can be used as is for administration to patients immediately, no adjustment to isotonicity being required, or stored at 5° C. for periods up to two years and longer.

Alternatively, the inclusion complex of ziprasidone in cyclodextrin can first be isolated by drying, usually by lyophilization. The isolated dry indusion complex can be stored at room temperature for periods up to two years and longer, and reconstituted into a product solution as needed. When a product solution is required, it can be made by dissolving the isolated inclusion complex in water (or other aqueous medium) in an amount sufficient to generate a solution of the required strength for oral or parenteral administration to patients. If parenteral administration is the chosen route of administration, intramuscular injection is preferred.

Solubility testing of various ziprasidone salts in, as example cyclodextrins, SBECD and HPBCD, was conducted by comparing the equilibrium solubility of each salt in an equal amount of aqueous cyclodextrin. Many different experimental protocols can be envisioned and implemented. The following protocol illustrates the protocol employed for the instant invention using 40% aqueous cyclodextrin. The same protocol was employed for other aqueous cyclodextrin concentrations such as those used to generate FIG. 1. HPBCD was purchased commercially from Wacker Chemie. The SBECD employed had a degree of substitution with sulfobutyl groups of 6.5, average, per molecule of β-cyclodextrin, made by a process along the lines of that described in Example 3 of U.S. Pat. No. 5,376,645.

A 40% (w/v) solution of cyclodextrin (SBECD or HPBCD) in water was prepared by adding 200 g of cyclodextrin to a 500 ml beaker containing approximately 250 ml of deionized water and a magnetic stir bar. The contents were stirred until dissolution of the cyclodextrin in the water was complete, usually a time of about one hour being sufficient. The solution was then transferred to a 500 ml volumetric flask and deionized water was added to the mark. 5 ml of the volumetric solution was pipetted into a 10 ml glass vial with a screw cap. An excess of the solid ziprasidone salt test candidate and a magnetic stir bar were added to the vial. The vial contents were stirred for four days at ambient temperature to allow a sufficient time for equilibrium to be established. Upon removal from the magnetic stirrer, the sample had undissolved solid present, indicating a saturated solution under the conditions employed. The contents were filtered into a clean screw cap vial through a Millex-GS 0.2 μm filter and the drug concentration determined by an HPLC method.

As an example of an HPLC assay to determine ziprasidone solubility, the amount of dissolved ziprasidone can be determined by using a C18 Puresil (Registered Trademark of Waters Associates) column with an isocratic mobile phase consisting of 60% 0.05 M potassium dihydrogen phosphate buffer and 40% methanol, at a flow rate of 2 ml/min at 40° C. Detection can be by UV absorption at a wavelength of 229 nm. Quantification can be effected facilely by comparison of HPLC peak height (or area) with the peak height (or area) taken from a standard plot of concentration vs. peak height (or area) for standards of known concentration. As is conventional, the ziprasidone standard concentrations are selected to fall within a linear range of concentration vs absorbance for the UV detector employed. The saturated equilibrium solution obtained after filtering the vial test solution may need to be diluted in serial fashion to reach the linear range of the standard plot, and dilution can be effected by adding isocratic mobile phase.

The above procedure was also employed to determine the equilibrium solubility of ziprasidone salts in other concentrations of cyclodextrin. By doing this and using the data to make solubility phase diagrams for different ziprasidone salts, it was determined that the solubility phase diagrams were linear for each salt, but that the slopes were different, thereby demonstrating that different ziprasidone salts can have different equilibrium solubilities in the same cyclodextrin solution. The solubility phase diagram generated by doing this for different ziprasidone salts is shown in FIG. 1.

Using the above HPLC procedure (including the column and isocratic mobile phase) a number of ziprasidone salts were tested to determine the equilibrium solubility of each in 40% HPBCD and in 40% SBECD. Results are reported in Table 1.

TABLE 1

Solubility of ziprasidone salts in water and 40% cyclodextrin solutions.

| Salt form | Solubility in water | Solubility in 40% HPBCD | Solubility in 40% SBECD |
|---|---|---|---|
| free base | 0.3 μgA/ml | 0.26 mgA/ml | 0.35 mgA/ml |
| tosylate | 5 μgA/ml | NT | 14 mgA/ml |
| napsylate | 34 μgA/ml | NT | 14 mgA/ml |
| besylate | 80 μgA/ml | NT | 12 mgA/ml |
| hydrochloride | 80 μgA/ml | 2.4 μgA/ml | 4 mgA/ml |
| aspartate | 170 μgA/ml | 1.3 μgA/ml | 9.3 mgA/ml |
| tartrate | 180 μgA/ml | 12.4 μgA/ml | 26 mgA/ml |
| esylate | 360 μgA/ml | 13.7 μgA/ml | 15 mgA/ml |
| mesylate | 1000 μgA/ml | 17.3 μgA/ml | 44 mgA/ml |

Note: μgA and mgA indicate the weight (in pg or mg respectively) of ziprasidone calculated as the free base, Molecular weight = 412.9; NT = Not tested
Molecular weight of β-cyclodextrin sufobutyl ether (SBECD): 2163; 40% (w/v) = 400 g/L = 0.18 M;
Molecular weight of hydroxy propyl β-cyclodextrin (HPBCD): 1309; 40% (w/v) = 400 g/L = 0.31 M Table 1 indicates that for the particular ziprasidone salt candidates and cyclodextrin solutions tested, the highest solubility of ziprasidone can be achieved by dissolving ziprasidone mesylate in 40% SBECD. To deliver a therapeutic dose of ziprasidone, for example, of 80 mg/day of ziprasidone to a patient, for example by injection, the volume of 40% solution needed can be calculated as follows:

80 mgA/day×1 ml/44 mgA=1.8 ml/day

Thus the instant invention provides therapeutically useful ziprasidone salt inclusion complexes. That is inclusion complexes which deliver a desired therapeutic dose of ziprasidone in an injection volume of less than 2 ml, can be determined.

As seen from FIG. 1, ziprasidone salt solubility is linear as a function of cyclodextrin concentration in water. Thus the maximum amount of a particular ziprasidone salt which can be dissolved in an aqueous cyclodextrin can be measured as known in the art directly from such a solubility phase diagram (i.e., employing the appropriate line as a calibration plot), or calculated if the slope (and y-intercept, if it is non-zero) of the appropriate line has been computed.

As previously mentioned, the inclusion complex can be formulated for oral or for parenteral administration, usually intramuscular administration, to a patient. Subcutaneous, intravenous and intranasal administration is also feasible. If necessary to adjust isotonicity, it can be accomplished conventionally by adding an isotonicity adjusting agent. Product solutions, as previously defined, can be used directly for parenteral administration. Dry mixtures of ziprasidone plus cyclodextrin can be sold as a unit dose packet for use by dissolution in water for oral administration. Dry mixtures of ziprasidone plus cyclodextrin, plus a dry filler if needed, can be used as fill for making capsules. Mixtures of ziprasidone plus cyclodextrin, optionally plus excipients such as binders, fillers, and lubricants, as known in the art, can be conventionally used to make tablets with conventional presses.

The following examples further disclose and illustrate the invention:

EXAMPLE 1

A 300 mg/ml SBECD solution is prepared by dissolving SBECD in a pharmaceutically acceptable aqueous medium such as water. Ziprasidone mesylate is dissolved in the SBECD solution to make a concentration of 27.3 mg/ml (20 mgA/ml). The solution is sterile filtered through a 0.2 μm filter. Glass vials are filled with the filtered solution to make a product solution which can be administered orally or by an intramuscular, intravenous, or subcutaneous route.

EXAMPLE 2

A product solution is made as described in Example 1. Glass vials containing product solution are loaded into a freeze dryer and the product solution is freeze dried. The vials and their lyophilized contents are stored at room temperature until needed, at which time they are reconstituted with sterile water or a pharmaceutically acceptable aqueous buffer for administration orally or by an intramuscular, intravenous, or subcutaneous route.

The following examples illustrate how to calculate dosage levels for particular inclusion complexes to deliver a particular dose, and also how to minimize injection volume.

EXAMPLE 3

Formulation I: ziprasidone mesylate 40 maA/ml in 40% (w/v) SBECD

Table 1 indicates that for a 20 mgA dose, about 0.5 ml of solution should be injected. For a maximum dose, 1.8 ml should be injected.

EXAMPLE 4

Formulation II: Ziorasidone Tartrate 20 mQA/ml in 40% (w/v) SBECD

For a 20 mgA dose, 0.8 ml of solution should be injected.
For a 40 mgA dose, 1.5 ml of solution should be injected.
For a 60 mgA dose, 2.3 ml of solution should be injected.

EXAMPLE 5

Ziprasidone Mesylate 1 g of ziprasidone free base was added to 20 mL of isopropyl alcohol, followed by 140 mg of methanesulfonic acid. After a few minutes the slurry which formed thickened and lightened somewhat in color as it precipitated. The salt was harvested by filtration through a 5 μm polytetrafluoroethylene membrane.

EXAMPLE 6

Ziprasidone Esylate 1 g of ziprasidone free base was added to 45 mL of THF and 1 mL of water, and the mixture was heated to 60° C.

while stirring. The mixture was maintained at 60° C. for two hours, at which time all of the free base had dissolved. 156 mg of ethanesulfonic acid was added and stirring was maintained at 60° C. for two more hours. The mixture turned from light orange to hazy during this time, at which point heating was stopped and the salt started to precipitate. The mixture was allowed to cool to room temperature overnight while stirring continued. The salt was then harvested by filtration as in Example 5.

EXAMPLE 7

Ziprasidone Tartrate 1 g of ziprasidone free base was added to 60 mL of water and the resulting slurry was heated to 50° C. for 3 hours with stirring. 900 mg of L-tartaric acid was added. Heating at 50° C. and stirring were continued for 6 more hours, and then the mixture was stirred at 40° C. overnight. The solution was then allowed to cool and the salt harvested as in Example 5.

What is claimed is:

1. A salt selected from ziprasidone esylate, ziprasidone mesylate, and ziprasidone tartrate.
2. A salt as defined in claim 1, which is ziprasidone esylate.
3. A salt as defined in claim 1, which is ziprasidone mesylate.
4. A salt as defined in claim 1, which is ziprasidone tartrate.

* * * * *